United States Patent [19]

Lagrange et al.

[11] Patent Number: 5,496,543
[45] Date of Patent: Mar. 5, 1996

[54] PRODUCT BASED ON INORGANIC OR ORGANIC PARTICLES BEARING AN INDOLINE-BASED PRODUCT

[75] Inventors: Alain Lagrange, Chatou; Hervé Andrean, Paris; Alex Junino, Livry-Gargan, all of France

[73] Assignee: L'Oreal, Paris, France

[21] Appl. No.: 117,206

[22] PCT Filed: Dec. 29, 1993

[86] PCT No.: FR93/00031
   § 371 Date: Sep. 16, 1993
   § 102(e) Date: Dec. 29, 1993

[87] PCT Pub. No.: WO93/13745
   PCT Pub. Date: Jul. 22, 1993

[30] Foreign Application Priority Data

Jan. 16, 1992 [FR] France ................................. 92 00417

[51] Int. Cl.$^6$ ............................ A61K 7/032; A61K 7/027; A61K 7/02

[52] U.S. Cl. .................... 424/70.7; 424/45; 424/61; 424/63; 424/64; 424/70.1; 424/401; 424/499; 424/500; 424/501; 424/DIG. 5; 514/844

[58] Field of Search ..................... 424/401, 499, 424/500, 501, 61, 63, 64, 70.1, 70.7, 45, DIG. 5; 514/844

[56] References Cited

FOREIGN PATENT DOCUMENTS

| | | |
|---|---|---|
| 0379409 | 7/1990 | European Pat. Off. . |
| 0462857 | 12/1991 | European Pat. Off. . |
| 2207153 | 1/1989 | United Kingdom . |

Primary Examiner—Jyothsna Venkat
Attorney, Agent, or Firm—Jacobson, Price, Holman & Stern

[57] ABSTRACT

A mineral or organic particle-based product comprising an indoline product, a method for preparing same, and the use thereof in cosmetics. The product is a powder consisting of mineral or organic particles smaller than 200 microns, and comprises, in and/or on the particles, an indoline product obtained by oxidative polymerization using at least one indoline.

21 Claims, No Drawings

PRODUCT BASED ON INORGANIC OR ORGANIC PARTICLES BEARING AN INDOLINE-BASED PRODUCT

The present invention relates to a product in the form of inorganic or organic particles containing an indoline-based product in or on the particles to a process for preparing it and to its use in cosmetics, in particular for making up the exoskeleton and/or the skin and protecting the human epidermis against UV radiation.

Pigments based on metal compounds, such as, for example, black and brown iron oxides, are generally used in makeup compositions for the skin and the exoskeleton. These pigments are not, however, completely harmless, and pigments capable of presenting fewer problems in their cosmetic application are consequently sought.

It is also desired, on some occasions, to be able to impart to the hair a coloration which can, if necessary, be removed very rapidly.

The Applicant has just discovered that it was possible to prepare in vitro a product in the form of a powder composed of inorganic or organic particles containing, in and/or on the particles, one or more indoline-based products resulting from the oxidative polymerization of at least one compound of the indoline family defined below.

He discovered that the use of this product in particle form was especially advantageous in as much as these particles, when introduced into a cosmetically acceptable medium, distribute well in then composition, which spreads readily on the exoskeleton or the skin and displays considerable covering power.

He also found that the product thereby obtained possessed an especially advantageous coefficient of absorption of ultraviolet radiation.

Lastly, the presence of indoline-based product, resulting from the oxidative polymerization of at least one indoline compound, makes it possible to obtain colorations of the final product which are especially advantageous in their use in cosmetics, inasmuch as the colorations capable of being obtained with the pigments which were available and compatible with cosmetic application were relatively limited. The colorations thereby obtained are especially stable to light.

The term "indoline-based product" or "indoline-based polymer" will be used hereinafter to denote the product obtained by oxidation of at least one indoline defined below.

The subject of the present invention is hence a powder consisting of inorganic or organic particles containing an indoline-based product in and/or on the particles.

Another subject of the invention consists of the preparation of such a powder.

The subject of the invention is also the cosmetic application of such powders, in particular in products for making up the skin and the exoskeleton and for protecting the human epidermis against UV radiation.

The term "exoskeleton" according to the invention will be used to denote the hair, hairs such as eyelashes and eyebrows and the nails.

Other subjects of the invention will become apparent on reading the description and examples which follow.

The product according to the invention is essentially characterized in that it takes the form of a powder consisting of inorganic or organic particles whose largest dimension is less than 200 microns and which contains, in and/or on the particles, a synthetic indoline-based product formed in situ by oxidative polymerization of at least one indoline.

The indoline-based product results from the oxidation of at least one compound of the indoline family, corresponding to the formula:

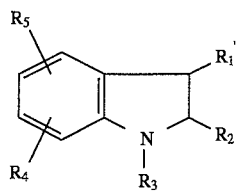

in which:

$R_1$ and $R_3$ represent, independently of one another, a hydrogen atom or a $C_1$–$C_4$ alkyl group;

$R_2$ represents a hydrogen atom, a $C_1$–$C_4$ alkyl group or a carboxyl or ($C_1$–$C_4$ alkoxy) carbonyl group;

$R_4$ denotes a hydrogen atom or a $C_1$–$C_4$ alkyl, hydroxyl, ($C_1$–$C_4$ alkoxy), amino or $C_1$–$C_{10}$ alkylamino or halogen group;

$R_5$ denotes a hydrogen atom or a hydroxyl, $C_1$–$C_4$ alkoxy or amino group;

at least one of the radicals $R_4$ or $R_5$ denoting a hydroxyl, alkoxy or amino group; with the proviso that when $R_5$ denotes an amino group, $R_4$ cannot denote an alkylamino radical;

$R_4$ and $R_5$ can also form a $C_1$–$C_2$ alkylenedioxy ring, and are at positions 5 and 6;

as well as the corresponding salts.

Among the compounds corresponding to the formula (I), the preferred compounds used according to the invention are chosen from 5,6-dihydroxyindoline, 6-hydroxy indoline, 5,6-methylenedioxyindoline, 7-methoxy-6-hydroxy indoline, 6,7-dihydroxyindoline, 5-hydroxy-4-methoxy indoline, 4,5-dihydroxyindoline, 5-methoxy-6-hydroxy indoline, 4-hydroxy-5-methoxyindoline, 5-hydroxy-6-methoxy indoline, 4,7-dihydroxyindoline, 6-aminoindoline, N-ethyl-4-hydroxyindoline, 1-ethyl-6-amino-indoline, 5,6-diaminoindoline, 1-methyl-6-aminoindoline, 2-methyl- 6-aminoindoline, 3-methyl-6-aminoindoline, 2-methyl-5,6-diaminoindoline, 5-chloro-7-aminoindoline, 3-methyl-5,7-diaminoindoline, 5,7-diaminoindoline, 2-methyl-5,7-diaminoindoline, 7-aminoindoline, 2-methyl-7-amino indoline, 4-aminoindoline, 4-amino-6-chloroindoline, 4-amino- 6-iodoindoline, 4-amino-5-bromoindoline, 4-amino-5-hydroxyindoline, 4-amino-7-hydroxyindoline, 4-amino-5-methoxyindoline, 4-amino-7-methoxyindoline, 5-amino indoline, 2,3-dimethyl-5-aminoindoline, 1-methyl-5-aminoindoline, 2-methyl-5-aminoindoline, 5-[N-(1-methyl hexyl)amino]indoline, 5,6-dimethoxyindoline and 5,6-dihydroxy-2-carboxyindoline.

The salts of the abovementioned compounds are cosmetically acceptable salts, chosen especially from the hydrochlorides, hydrobromides, sulfates and methanesulfonates. The hydrobromides of the above compounds are especially preferred.

The indoline-based products can also result from the cooxidation of at least one defined indoline and at least one indole derivative. The latter may be chosen from mono- and dihydroxyindoles or aminoindoles as are described, more especially, in Patent EP-A-239,826 and Patent Applications EP-A-425,345 and GB-A-2,224,754.

These indoles correspond, more especially, to the formula:

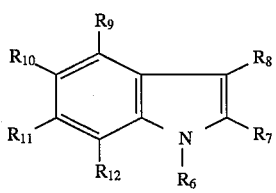

(II)

in which:

$R_6$ and $R_8$ denote, independently of one another, a hydrogen atom or a $C_1$–$C_4$ alkyl group;

$R_7$ represents a hydrogen atom, a $C_1$–$C_4$ alkyl group, a carboxyl group or a ($C_1$–$C_4$alkoxy)carbonyl group;

$R_9$ and $R_{12}$ denote, independently of one another, a hydrogen atom, a hydroxyl group or a $C_1$–$C_4$ alkyl, amino, ($C_1$–$C_4$ alkoxy), ($C_2$–$C_4$ acyl)oxy or ($C_2$–$C_4$ acyl)amino group;

$R_{10}$ denotes hydrogen or a hydroxyl, ($C_1$–$C_4$ alkoxy), ($C_1$–$C_4$ alkyl), halogen, amino, ($C_2$–$C_{14}$ acyl)oxy, ($C_2$–$C_4$acyl)amino or trimethylsilyloxy group;

$R_{11}$ denotes hydrogen or a hydroxyl, ($C_1$–$C_4$ alkoxy), amino, ($C_2$–$C_4$ acyl) oxy, ($C_2$–$C_4$ acyl)amino, trimethylsilyloxy or hydroxy($C_2$–$C_4$ alkyl)amino group;

$R_{10}$ and $R_{11}$, together with the carbon atoms to which they are attached, can form a methylenedioxy ring optionally substituted with a $C_1$–$C_4$ alkyl or $C_1$–$C_4$ alkoxy group or a carbonyldioxy ring;

at least one of the groups $R_9$ to $R_{12}$ represents a group OZ or NHR, not more than one of the groups $R_9$ to $R_{12}$ denoting NHR;

and not more than two of the groups $R_9$ to $R_{12}$ denote OZ, in the case where Z denotes hydrogen, these groups are at positions 5 and 6;

and at least one of the groups $R_9$ to $R_{12}$ represents hydrogen, in the case where only one of these groups denotes hydrogen, only one group from among $R_9$ to $R_{12}$ then denotes NHR or OZ and the other groups denote $C_1$–$C_4$ alkyl; R in NHR denoting a hydrogen atom or a $C_2$–$C_4$ acyl or $C_2$–$C_4$ hydroxyalkyl group, and Z in OZ denoting a hydrogen atom or a $C_2$–$C_{14}$ acyl, $C_1$–$C_4$ alkyl or trimethylsilyl group; and the corresponding salts.

The indoles are chosen from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl - 5,6-dihydroxyindole, 2,3-dimethyl- 5,6-dihydroxy-indole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy- 5-ethoxy-N-methylindole, 6-hydroxy-5-methoxy-2-methylindole, 6-hydroxy-5-methoxy-2,3-dimethylindole, 6-hydroxy 2-ethoxycarbonylindole, 7-hydroxy-3-methylindole, 5-hydroxy- 6-methoxy-2,3-dimethylindole, 5-hydroxy-3-methyl indole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-[N-(β-hydroxyethyl)amino]indole, 4-aminoindole, 5-aminoindole, 6-aminoindole, 7-aminoindole, N-methyl-6-(β-hydroxyethylamino)indole, 6-amino-2,3-dimethylindole, 6-amino-2,3,4,5-tetra-methylindole, 6-amino-2,3,4-trimethylindole, 6-amino- 2,3,5-trimethylindole, 6-amino-2,3,6-trimethylindole, 5,6-diacetoxyindole, 5-methoxy-6-acetoxyindole and 5,6-dimethoxyindole.

In the cooxidation, it is possible to use up to 50 mol % of indole derivatives relative to the total number of moles of derivatives to be oxidized.

The particles used according to the invention are inorganic particles in lamellar or non-lamellar form or lamellar or non-lamellar organic particles, which are colored or uncolored. These particles have an average particle size of between 0.01 and 200 microns.

The non-lamellar inorganic particles which can be used according to the invention are inert inorganic particles having a particle size of less than 20 microns, and preferably less than 10 microns, and more especially less than or in the region of 5 microns.

Such particles are, in particular, chosen from calcium carbonate, silica or titanium oxide particles having the particle size defined above.

The lamellar particles used according to the invention are inorganic or organic particles which take the form of lamellae, where appropriate stratified.

These lamellae are characterized by a thickness which is smaller than the largest dimension. Preferably, the ratio between the largest dimension and the thickness is between 2 and 100. The largest dimension is generally less than 50 microns.

The particles of lamellar structure are chosen especially from the following products: L-lauroyllysine such as the product sold under the name AMIHOPE L.L by the company AJINOMOTO; microparticles of ceramic which are optionally coated with zirconiumpowder, such as the products sold under the names TORAYCERAM ZP 550 and ZP 4000 by the company TORAY; lamellar titanium dioxide such as the products sold under the names LUXELEN SILK D and LUXELEN SS by the company SUMITOMO, lamellar talc, boron nitride such as the products sold under the names Boron Nitride SF or SHP by the companies WACKER and KAWASAKI; lamellar mica such at the product sold under the name MICA CONCORD 1000 by the company SCIAMA; bismuth oxychloride such as the product sold under the name PEARL GLO by the company MALLINCKRODT; and transparent red iron oxide such as the product sold under the name CAPPOXYT 4435 B by the company CAPPELLE.

The size of the particles of lamellar structure used according to the invention is preferably less than 50 microns, and especially less than 25 microns. Their size is generally greater than 0.5 micron. It is, in particular, between 1 and 20 microns. These particles are generally greater than 0.01 micron in thickness. As stated above, these lamellar particles can take the form of a stratified structure.

It is also possible to use colored particles according to the invention. They are colored, non-white inorganic particles consisting of metal salts which are insoluble in the cosmetic medium and usable in cosmetics, referenced in the Color Index under the section "Inorganic Coloring Matters" and which bear the numbers 77000 to 77947, excluding the white pigments. These colored inorganic particles can consist of a single pigment or a mixture of pigments. They can also take the form of nacreous or interference pigments.

The colored inorganic particles are preferably chosen from iron oxides, ultramarine blue (which is a complex sulfosilicate), chromium oxides, manganese violet (which is an ammonium manganese pyrophosphate) and Prussian blue (which is an iron ferricyanide).

The size of the particles of the colored powder, using colored inorganic particles containing the indoline-based product, depends on the size of the colored particles used, and can vary within wide limits ranging from 0.01 to 150 microns.

Thus, when the starting colored inorganic particle is a nacreous or interference pigment, the size of the powder particles according to the invention varies between 10 and 150 microns.

In contrast, when the colored inorganic particle is a metal salt (iron or chromium oxides, iron or manganese salts), the size of the powder particles according to the invention is generally between 0.01 and 5 microns.

The non-lamellar organic particles used according to the invention are fine particles of polymers. The product obtained with these organic particles according to the invention is characterized in that it consists of polymer particles having a particle size of less than 100 microns and which contain, at the surface and/or in the polymer network, an indoline-based product resulting from the oxidative polymerization of at least one compound of the indoline family corresponding to the formula (I) defined above and, where appropriate, from a cooxidation with an indole compound.

The size of these organic particles is generally greater than 0.01 micron, and preferably between 0.01 and 50 microns, and especially between 0.1 and 20 microns. They are preferably spherical.

The polymers which can be used according to the invention are polymers which are essentially insoluble in the reaction medium, and are chosen from natural or synthetic, organic or inorganic polymers comprising a crystalline or amorphous crosslinked network and having a molecular weight of between 5000 and 5,000,000.

The essentially insoluble character of the polymer is justified on essentially economic grounds, inasmuch as the indoline-based product must bind to a solid particulate carrier in order to form the product according to the invention.

The solubility of the polymers in the reaction medium should preferably not exceed 10%.

The organic or synthetic polymers are chosen especially from polymers derived from keratin, from chitin or from cellulose and polyamides, or homo- or copolymers. resulting from the polymerization of aliphatic or aromatic mono- or polyethylenic monomers comprising a crystalline or amorphous crosslinked network.

The polymers derived from keratin are chosen especially from animal or human keratins originating, for example, from materials chosen from hair, wool, skin, hairs, silks, feathers, scales and more especially hooves, horn or alternatively silk fibroin.

These materials are preferably washed and/or degreased, and then reduced to particles.

Other polymers derived from keratin are chemically modified keratins having a molecular weight of between 10,000 and 250,000, and especially the partially hydrolyzed keratin (or keratinhydrolysate) obtained from skins which are rich in sulfur-containing products and have a molecular weight of between 50,000 and 200,000. This hydrolysate is preferably obtained by moderate alkaline hydrolysis.

Products of this type are, for example, sold under the name KERASOL by the company CRODA.

Other modified keratins are sulfonic keratins of molecular weight between 10,000 and 100,000, obtained from goose or chicken feathers or, still more advantageously, from hooves or horn.

This keratin is obtained by oxidation of all or part of the disulfide bonds of the cystine groups of keratin to cysteic acid groups: $SO_3H$, the oxidation being advantageously performed in an acid medium such as formic acid, by means of an oxidizing agent such as hydrogen peroxide.

The polymers derived from chitin consist of chitin which is a natural polymer, the largest source of which is in the shell of shellfish such as crabs, lobsters, crayfish, and the like. The chitin is prepared according to a process described, in particular, in the work of R.A.A. MUZZARELLI "CHITIN", published by PERGAMON PRESS OXFORD, 1977, pages 89–100 and 207–217. It is also possible to use its deacetylated derivative known by the name of chitosan, obtained by hydrolysis of the acetyl groups of chitin.

Chitosan as available commercially is partially acetylated and contains 70 to 90% by weight of chitosan. It is also possible to use it in the form of its insoluble salts such as the sulfates and phosphates. Products of this the are sold, for example, under the name KYTEX by the company HERCULES.

The cellulose polymers are chosen more especially from microcrystalline celluloses such as the products sold under the name AVICEL by the company FMC.

Among synthetic polymers, very special mention may be made of polyethylene, polyloropylene, polystyrene, poly(methyl methacrylate) and crosslinked poly(methyl methacrylate) such as the product sold under the name MICROPEARL M 305 by the company SEPPIC. Other polymers are chosen especially from crosslinked poly-β-alanine, as described in French Patent 2,530,250 or else advantageously taking the form of microspheres possessing a very low size dispersity, 85% by weight having a particle size of between 28 and 46 microns. These poly-β-alanines are obtained according to a process which consists in polymerizing acrylamide in a t-butanol/toluene solvent mixture in ratios of between 1:24 and 10:1, and preferably between 1:6 and 6:1, at between 60° and 100° C., and preferably at about 80° C., in the presence of a polymerization initiator and of an octadecene/maleic anhydride copolymer as suspending agent, and then in subjecting the poly-β-alanine suspension obtained to a crosslinking using a dialdehyde such as glutaraldehyde.

The polymerization initiator is preferably sodium tert-butylate or potassium tert-butylate (0.1 to approximately 2 mol % relative to the acrylamide).

Glutaraldehyde is used in the form of an aqueous solution of between 20 and 25%, and in a proportion of between 1 and 15% by weight relative to the weight of starting acrylamide.

As polymers, it is also possible to use products known by the name of microsponges, such as styrene/divinylbenzene or methyl methacrylate/ethylene glycol dimethacrylate or vinyl stearate/divinylbenzene crosslinked polymers as described in Patents WO-88/01,164 and U.S. Pat. No. 4,690,825.

Such polymers consist essentially of beads of crosslinked polymers containing an internal pore network capable of retaining the indoline-based product.

Other polymers of this type are hollow microspheres of a copolymer of vinylidene chloride and acrylonitrile, sold under the name EXPANCEL by the company KEMA NORD; and porous microspheres of polyamide 12, polyamide 6 or copolyamide 6/12, sold under the name ORGASOL by the company ATO-CHIMIE. These microspheres preferably have a particle size of between 10 and 50 microns.

It is also possible to use silicone powders which are gums, resins and more especially organosiloxane elastomers.

The products according to the invention may be prepared according to a process which consists essentially in mixing in the air, and at a temperature which is preferably room temperature and can range up to 100° C., at least one indoline compound of formula (I) and the inorganic or organic particles described above, in a medium which is essentially a non-solvent for the particles.

The oxidation of the indoline compound of formula (I) may be performed in an aqueous or water/solvent medium, in the air, in the air in the presence of an alkaline agent and/or of a metal-based oxidation catalyst such as cuptic ion.

If no oxidizing agent other than aerial oxygen is used, it is preferable to work at an alkaline pH, in which case the pigment forms gradually and binds to the surface of the particles and/or in the network or the pores of the particles.

These products may also be prepared by carrying out an immediate formation of the indoline-based product using an oxidizing agent such as hydrogen peroxide, peracids and persalts.

It is preferable to use periodic acid and its derivatives and water-soluble salts, organic peracids and their salts, permanganates and dichromates such as those of sodium or potassium, sodium hypochlorite, potassium ferricyanide, ammonium persulfate, alkali metal chlorites, silver oxide, ferric chloride, lead oxide, sodium nitrite and rare-earth salts such as those of cerium.

It is also possible to use organic oxidizing agents chosen from ortho- and para-benzoquinones, ortho- and para-benzoquinone monoamines and diimines, 1,2- and 1,4-naphthoquinones and 1,2- and 1,2-naphthoquinone monoor diimines. The oxidation may also be performed by the addition of iodide and hydrogen peroxide, the iodide preferably being an alkali metal, alkaline-earth metal or ammonium iodide.

The preferred periodic acid salt is sodium periodate.

These oxidizing agents may be activated, where appropriate, with a pH-modifying agent.

For the products intended for cosmetic application, it is preferable to use hydrogen peroxide, periodic acid and its salts, potassium permanganate, sodium hypochlorite, ammonium persulfate, sodium nitrite and the iodide/hydrogen peroxide system as oxidizing agents.

The order of addition of the compounds participating in the preparation of the product in particle form, according to the invention, is of little importance provided that the oxidizing agent is incorporated last when the latter is used without a pH-modifying agent and, in the case of the iodide/hydrogen peroxide oxidizing system, either hydrogen peroxide or the iodide is introduced last.

It is also possible to carry out enzymatic oxidation, carrying out oxidation using an enzyme having oxidizing or peroxidizing activity, such as horseradish peroxidase, chloroperoxidase, milk peroxidase and cytochrome C peroxidase, or peroxidizing enzymes, in particular hemoglobin, methemoglobin, myoglobin and metmyoglobin. This enzymatic oxidation may also be performed in the presence of tyrosinase with aerial oxygen.

In the case where a pH-modifying agent is used to activate the oxidizing agent, it is preferable to add either the oxidizing agent or the pH-modifying agent last.

When a keratin hydrolysate is used as an organic particle, the pH of the medium can preferably be below 5 in order to avoid solubilization of the modified keratin.

When a sulfonic keratin is used, the medium is either essentially alcoholic, or aqueous, in which case the pH should be below 7.

When chitosan is used, the aqueous medium should preferably have a pH above 5.8.

The reaction medium used should be a medium which is essentially a non-solvent for the organic or inorganic particle in question. It preferably consists of water, and can optionally consist of a mixture of water and one or more solvents such as $C_1$–$C_4$ lower alcohols, for instance ethyl alcohol, propyl or isopropyl alcohol and tert-butyl alcohol, alkylene glycols such as ethylene glycol and propylene glycol, alkylene glycol alkyl ethers such as ethylene glycol monomethyl, monoethyl and monobutyl ethers and propylene glycol and dipropylene glycol monomethyl ethers, and methyl lactate.

The medium must, moreover, be able to solubilize the indoline compound and, where appropriate, the indole derivative or derivatives.

When the medium consists of a water/solvent(s) mixture, the solvent(s) is/are present in concentrations preferably of between 0.5 and 95% by weight relative to the total weight of the composition, and especially between 2 and 50% by weight, and preferably between 2 and 20% by weight.

Their nature is chosen and their proportion is adjusted in accordance with the criteria of solubility of the derivatives of the family of the indolines (I) defined above, and, where appropriate, of the indoles of formula (II) in the case of cooxidation, and with the criterion of insolubility of the inorganic or organic particles employed.

In the process according to the invention, it is preferable to use the compounds of the indoline family in weight proportions of between 0.1 and 10%, and preferably between 0.5 and 7%, by weight, the inorganic or organic filler representing 0.075 to 70% by weight, and preferably 4 to 50% by weight, relative to the weight of the reaction medium, the remainder of the mixture generally consisting of water or a water/solvent mixture.

The oxidizing agents are employed in amounts sufficient to oxidize the compound of the family of the indolines of the formula (I), and, where appropriate, to cooxidize the indoline compound of the formula (I) and the indole compound of the formula (II), to form the indoline-based product on or in the inorganic or organic particles.

When iodide ion is used to form the indoline-based product, it is preferably used in proportions of 0.07 to 4%, and especially between 0.7 and 3%, observing a ratio of indoline compound and, where appropriate, indole derivative to iodide ions of between 0.6 and 6.

The proportions are determined relative to the weight of the reaction medium. When it is desired to carry out a cooxidation of one or more indoline derivatives of the formula (I) with one or more indole derivatives of the formula (II), the procedure is the same, simply mixing before oxidation of the derivatives to be oxidized.

The product based on particles containing the indoline-based product in and/or on the particle, according to the invention, is used in cosmetics, more especially in compositions for making up the skin and/or the exoskeleton and for protecting the human epidermis.

The powder in the form of inorganic or organic particles and containing the indoline-based product as defined above may be added to conventional cosmetic carriers at a concentration of between 0.05 and 35%, and preferably between 0.5 and 20%, by weight relative to the total weight of the composition, to yield cosmetic compositions for protecting the human epidermis, makeup products such as those for making up the eyelashes, eyebrows, skin, hair or nails, for instance eyeshadows, blushers, lining products also known as eyeliners, mascaras for the eyelashes and eyebrows, and nail varnishes, or alternatively compositions for the temporary dyeing of hair. These cosmetic carriers are known per se.

The medium used in these various cosmetic compositions is a medium which is essentially a non-solvent for the inorganic or organic particles containing the indoline-based product.

The term "medium which is essentially a nonsolvent" is used to denote a medium which dissolves less than 1% by weight of the inorganic or organic particles containing the indoline-based product.

The compositions can take the form, in particular, of a lotion, thickened lotion, gel, cream, milk, powder or stick, and can optionally be packaged as an aerosol and take the form of a foam or spray.

When the compositions are used for making up the skin, hair, eyelashes and eyebrows, they can, in particular, take anhydrous or aqueous pasty or solid form, for example oil-in-water or water-in-oil emulsions or alternatively suspensions. These compositions have the advantage of being stable and of affording complete safety.

When the compositions are used for protecting the human epidermis against UV radiation, they constitute so-called "sun" compositions, and they can take the form of suspensions or dispersions in solvents or fats, or alternatively in the form of emulsions such as creams and milks, ointments, gels, solid sticks or aerosol foams.

In all cases, when they are used in the form of emulsions, they can contain, in addition, surfactants which are well known in the prior art, such as anionic, nonionic, cationic or amphoteric surfactants.

The makeup compositions and the sun compositions can also contain fats, organic solvents, silicones, thickeners, demulcents, sunscreen agents, antifoams, hydrating agents, perfumes, preservatives, antioxidants, fillers, sequestering agents, treatment agents such as anionic, cationic, nonionic or amphoteric polymers or mixtures thereof, propellants and alkalinizing or acidifying agents.

The fats can consist of an oil or a wax or a mixture thereof, fatty acids, fatty alcohols, petroleum jelly, paraffin, lanolin, hydrogenated lanolin or acetylated lanolin.

The oils are chosen from animal, vegetable, mineral or synthetic oils, and in particular hydrogenated palm oil, hydrogenated castor oil, liquid paraffin, paraffin oil and Purcellin oil.

The waxes are chosen from animal, fossil, vegetable, mineral or synthetic waxes. Special mention may be made of beeswax, carnauba, candellila [sic], sugar cane and Japan waxes, ozokerites, montan wax, microcrystalline waxes and paraffins.

When the compositions are used for coloring the nails, they take the form of products termed "nail varnishes" containing the powder according to the invention in dispersed form in a cosmetically acceptable solvent containing one or more resins, and ingredients customarily used in this type of product.

The compositions according to the invention can also contain, in addition to the inorganic or organic particles containing the indoline-based product as is defined above, other pigments which are generally used in cosmetics, in particular nacreous and/or pearlescent, colored or white pigments which make it possible to vary the colorations capable of being obtained or to increase the protection with respect to ultraviolet radiation. In the latter case, it is preferable to use nanopigments of metal oxides such as titanium, zinc, cerium or zirconium oxides, of average diameter less than 100 nm and preferably between 5 and 50 nm. The pigments may be coated or uncoated.

The coated pigments are pigments which have undergone one or more surface treatments of a chemical, electronic, mechanochemical and/or mechanical nature with compounds such as those described, for example, in COSMETICS & TOILETRIES, February 1990, Vol. 105, pages 53–64, such as amino acids, beeswax, fatty acids, fatty alcohols, anionic surfactants, lecithins, sodium, potassium, zinc, iron or aluminum salts of fatty acids, metal alkoxides (of titanium or aluminum), polyethylene, silicones, proteins (collagen, elastin), alkanolamines, silicon oxides, metal oxides or sodium hexametaphosphate.

The subject of the invention is also a process for the temporary dyeing of hair, making up the skin, eyelashes and eyebrows or nails and protecting the human epidermis against the deleterious effects of UV radiation, employing a powder based on inorganic or organic particles containing indoline-based products as defined above, this powder being applied directly or by means of cosmetic compositions as defined above.

The examples which follow are intended to illustrate the invention, no limitation, however, being implied thereby.

PREPARATION EXAMPLES

EXAMPLE 1

7.3 g (0.031 mol) of 5,6-dihydroxyindoline hydrobromide are solubilized in 100 ml of 0.1% aqueous ammonia solution. 45 g of polyamide 12 powder, sold under the name ORGASOL 2002 D Natural COS by the company ATOCHEM, are added to this mixture. This suspension is stirred for 15 minutes and then brought to 80° C. 10.5 ml of 3N sodium hydroxide are then added, and 28.6 g of hydrogen peroxide solution containing 2.3 g (0.067 mol) of hydrogen peroxide are added in the course of 30 minutes while the temperature is maintained at between 80° and 85° C. When the addition is complete, the temperature is maintained at 80° C. for 2 hours and the reaction medium is then cooled. The product is centrifuged and washed with water. After lyophilization, 42 g of gray-brown powder are obtained.

EXAMPLE 2

7.3 g (0.031 mol) of 5,6-dihydroxyindoline hydrobromide are solubilized in 100 ml of 0.1% aqueous ammonia solution. 45 g of boron nitride, sold under the name SHP2 by the company KAWASAKI, are added to this mixture. This suspension is stirred for 15 minutes and then brought to 80° C. 10.5 ml of 3N sodium hydroxide are then added, and 28.6 g of hydrogen peroxide solution containing 2.3 g (0.067 mol) of hydrogen peroxide are added in the course of 30 minutes while the temperature is maintained at between 80° and 85° C. The procedure is thereafter as in Example 1. After lyophilization, 41 g of bluish-gray powder are obtained.

EXAMPLE 3

7.3 g (0.031 mol) of 5,6-dihydroxyindoline hydrobromide are solubilized in 100 ml of 0.1% aqueous ammonia solution. 45 g of non-lamellar red iron oxide, which is a mixture of yellow iron oxide (CI77492) and brown iron oxide (CI77491), are added to this mixture. The procedure is thereafter as in Example 1. After lyophilization, 41 g of brown powder are obtained.

EXAMPLE 4

7.3 g (0.031 mol) of 5,6-dihydroxyindoline hydrobromide are solubilized in 100 ml of 0.1% aqueous ammonia solution. 45 g of ultramarine blue (CI77007) are added to this mixture. The procedure is thereafter as in Example 1. After lyophilization, 49 g of dark blue powder are obtained.

EXAMPLE 5

7.3 g (0.031 mol) of 5,6-dihydroxyindoline hydrobromide are solubilized in 100 ml of 0.1% aqueous ammonia solution. 45 g of hydrated chromium oxide (CI77289) are added to this mixture. The procedure is thereafter as in Example 1.

After lyophilization, 41.5 g of bluish-green powder are obtained.

EXAMPLE 6

7.3 g (0.031 mol) of 5,6-dihydroxyindoline hydrobromide are solubilized in 100 ml of 0.1% aqueous ammonia solution. 45 g of silica, sold under the name SILICA BEADS SB 150 by the company MAPRECOS, are added to this mixture. The procedure is thereafter as in Example 1. After lyophilization, 45.8 g of gray-brown powder are obtained.

EXAMPLE 7

7.3 g (0.031 mol) of 5,6-dihydroxyindoline hydrobromide are solubilized in 100 ml of 0.1% aqueous ammonia solution. 45 g of titanium oxide, sold under the name F. F. HOMBITAN by the company SACHTLEBEN, are added to this mixture. The procedure is thereafter as in Example 1. After lyophilization, 48.5 g of bluish-gray powder are obtained.

EXAMPLE 8

4.38 g (0.0188 mol) of 5,6-dihydroxyindoline hydrobromide and 2.19 g (0.0147 mol) of 5,6-dihydroxyindole are solubilized in 100 ml of 0.1 % aqueous ammonia solution. 45 g of ultramarine blue (CI77007) are added to this mixture. This suspension is stirred for 15 minutes and then brought to 80° C. 6.7 ml of 3N sodium hydroxide are then added, and 28.6 g of hydrogen peroxide solution containing 2.3 g (0.067 mol) of hydrogen peroxide are added in the course of 30 minutes while the temperature is maintained at between 80 and 85° C. When the addition is complete, the temperature is maintained at 80° C. for 2 hours and the reaction medium is then cooled. The product is centrifuged and washed with water. After lyophilization, 49 g of dark blue powder are obtained.

EXAMPLE 9

15.4 g (0.065 mol) of 5,6-dihydroxyindoline hydrobromide are solubilized in 190 ml of 0.1% aqueous ammonia solution and 10 ml of ethanol. 90 g of L-lauroyllysine are added to this mixture. This suspension is stirred for 15 minutes and then brought to 80° C. 6.6 ml of 3N sodium hydroxide are then added, and 15.1 g (0.13 mol) of hydrogen peroxide diluted in 45.3 g of water are added in the course of 30 minutes while the temperature is maintained at between 80° C. and 85° C. When the addition is complete, stirring is maintained and the temperature is maintained at 80° C. for approximately 2 hours and the reaction medium is then cooled. The product is centrifuged and washed with water. After lyophilization, 93 g of black powder are obtained.

EXAMPLE 10

13.95 g (0.06 mol) of 5,6-dihydroxyindoline hydrobromide are solubilized in 410 ml of 0.1% aqueous ammonia solution. 262 g of poly-β-alanine and also 50 ml of water are added to this mixture. This suspension is stirred for approximately 2 hours and then brought to 80° C. 6 ml of 3N sodium hydroxide are then added and the temperature is maintained at 80° C. for approximately 30 minutes. 13.82 g (0.12 mol) of hydrogen peroxide diluted in 41.46 g of water are then added in the course of 30 minutes while the temperature is maintained at between 80° C. and 85° C. When the addition is complete, the temperature is maintained at 80° C. and stirring is maintained for approximately 2 hours and the reaction medium is then cooled. The product is filtered off and washed with water. After lyophilization, 93.20 g of dark brown powder are obtained.

EXAMPLE 11

7.68 g (0,033 mol) of 5,6-dihydroxyindoline hydrobromide are solubilized in 195 ml of 0.1% aqueous ammonia solution. 95 g of bismuth oxychloride, sold under the name "PEARL GLOW UVR 1086" by the company MALLINCKRODT, are added to this mixture. 3.3 ml of 3N sodium hydroxide are then added. The mixture is stirred for approximately 15 minutes and the temperature is then brought to 80° C.

7.55 g (0.07 mol) of hydrogen peroxide diluted in 22.7 g of water are then added in the course of 30 minutes while the temperature is maintained at between 80° C. and 85° C. When the addition is complete, the temperature is maintained at 80° C. and stirring is maintained for approximately 2 hours and the reaction medium is then cooled. The product is centrifuged and washed with water. After centrifugation, 95.37 g of brown powder are obtained.

EXAMPLE 12

7.68 g (0,033 mol) of 5,6-dihydroxyindoline hydrobromide are solubilized in 195 ml of 0.1% aqueous ammonia solution. 95 g of powder consisting of an 83:17 mica/titanium mixture are added to this mixture. The procedure is thereafter as described in Example 11. After lyophilization, 88.21 g of metallic-gray powder are obtained.

EXAMPLE 13

15.4 g (0.065 mol) of 5,6-dihydroxyindoline hydrobromide are solubilized in 195 ml of 0.1% aqueous ammonia solution. 90 g of microbeads of acrylic polymer, sold under the name POLYTRAP by DOW CORNING, and also 10 ml of ethanol are then added to this mixture. The procedure is thereafter as described in Example 9. After lyophilization, 91.5 g of white powder are obtained.

FORMULATION EXAMPLES

EXAMPLE 1

A creamy mascara of the following formula is prepared:

| | |
|---|---|
| Triethanolamine stearate | 15.0 g |
| Beeswax | 8.0 g |
| Paraffin | 3.0 g |
| Colophony | 2.0 g |
| Ozokerite | 10.0 g |
| Propyl para-hydroxybenzoate | 0.20 g |
| Methyl para-hydroxybenzoate | 0.20 g |
| Gum arabic | 0.50 g |
| Keratin hydrolysate | 1.0 g |
| Black iron oxide | 5.0 g |
| Colored powder of Preparation Example 4 | 10.0 g |
| Water q.s. | 100 g |

The procedure is as follows:

The waxes are melted. The pigments are incorporated. The aqueous phase containing the preservatives, gum and keratin hydrolysate is heated to the same temperature as the waxy phase. The two phases are mixed and stirred vigorously. A dark blue mascara cream is obtained.

EXAMPLE 2

An eyelash makeup composition as follows is prepared:

| | |
|---|---|
| $C_8$–$C_{30}$ alkyl acrylate/acrylate crosslinked copolymer | 0.10 g |
| Crosslinked polyvinylcarboxylic polymer sold under the name CARBOPOL 940 by the company GOODRICH | 0.60 g |
| Triethanolamine | 0.80 g |
| Glycerol | 2.0 g |
| Preservative | 0.2 g |
| Octamethylcyclosiloxane | 25.0 g |
| Colored powder of Preparation Example 3 | 5.0 g |
| Black iron oxide | 5.0 g |
| Water q.s | 100 g |

The polymers are dispersed in the heated state with the preservatives in the water to make a gel. The glycerol and triethanolamine are added. The pigments are dispersed in the silicone and added to the gel phase. A black shiny gelled emulsion for making up the eyelashes is obtained.

EXAMPLE 3

A lipstick of the following composition is prepared:

| | |
|---|---|
| 2,6-Di-tert-butyl-p-cresol | 0.16 g |
| Liquid lanolin | 17.50 g |
| Microcrystalline wax | 15.0 g |
| Triglycerides of caprylic and capric acids | 11.0 g |
| Octylglyceryl behenate | 11.0 g |
| Colored powder of Preparation Example 3 | 3.0 g |
| Titanium mica | 6.0 g |
| Castor oil q.s. | 100 g |

A nacreous-brown lipstick is obtained.

EXAMPLE 4

A blusher of the following composition is prepared:

| | |
|---|---|
| Titanium dioxide | 10.0 g |
| Titanium mica | 10.0 g |
| DC Red 30 | 1.2 g |
| Propyl para-hydroxybenzoate | 0.2 g |
| Liquid paraffin | 6.0 g |
| 2-Hydroxy-4-methoxybenzophenone sold under the name UVINUL M40 by the company BASF | 0.5 g |
| Colored powder of Preparation Example 6 | 3.0 g |
| Talc q.s. | 100 g |

This beige-pink compacted blusher is applied with a brush.

EXAMPLE 5

An eye shadow of the following composition is prepared:

| | |
|---|---|
| Polyamide powder | 15.0 g |
| Cyclomethicone | 9.0 g |
| Titanium mica | 30.0 g |
| Colored powder of Preparation Example 5 | 7.0 g |
| Colored powder of Preparation Example 1 | 6.0 g |
| Talc q.s | 100 g |

This gray-green eyeshadow is applied with a brush or with a foam applicator.

EXAMPLE 6

A compact face powder of the following composition is prepared:

| | |
|---|---|
| Polyethylene powder | 5.0 g |
| Colored powder of Preparation Example 3 | 6.0 g |
| Titanium dioxide | 10.0 g |
| Mica | 12.0 g |
| Isopropyl myristate | 1.5 g |
| Liquid paraffin | 1.5 g |
| Sorbitol | 0.5 g |
| Colored powder of Preparation Example 7 | 3.0 g |
| Talc q.s. | 100 g |

This natural beige powder is applied with a powder puff or brush.

EXAMPLE 7

A makeup foundation for the face of the following composition is prepared:

| | |
|---|---|
| Glycerol stearate | 2.2 g |
| Mixture of capric and caprylic acids and glycerol triester | 15.0 g |
| Titanium oxide | 10.53 g |
| Yellow iron oxide | 0.83 g |
| Synthetic melanin pigment | 0.14 g |
| Colored powder of Example 3 | 0.50 g |
| Methyl para-hydroxybenzoate | 0.10 g |
| Propyl para-hydroxybenzoate | 0.10 g |
| Preservative | 0.3 g |
| 2-Hydroxy-4-methoxybenzophenone | 0.5 g |
| Octyl dimethyl-p-aminobenzoate | 0.5 g |
| Magnesium aluminum silicate | 1.0 g |
| Triethanolamine | 1.0 g |
| Carboxymethylcellulose | 0.16 g |
| Aluminum salt of the reaction product of octenylsuccinic anhydride and starch, sold under the name DRY FIO [sic] by the company NATIONAL STARCH | 5.0 g |
| Cyclic polydimethylsiloxane sold under the name SILBIONE OIL 70045 by the company RHONE POULENC | 10.0 g |
| Propylene glycol | 2.0 g |
| Glycerol | 3.0 g |
| Sodium lauroylsarcosinate | 0.6 g |
| Stearic acid | 2.2 g |
| Water q.s. | 100 g |

The makeup foundation obtained is natural beige.

EXAMPLE 8

A creamy mascara of the following composition is prepared:

| | |
|---|---|
| Triethanolamine stearate | 15.0 g |
| Beeswax | 8.0 g |
| Paraffin | 3.0 g |
| Colophony | 2.0 g |
| Ozokerite | 10.0 g |
| Propyl para-hydroxybenzoate | 0.20 g |
| Methyl para-hydroxybenzoate | 0.20 g |
| Gum arabic | 0.50 g |
| Keratin hydrolysate | 1.0 g |
| Black iron oxide | 5.0 g |
| Colored powder of Preparation Example 8 | 10.0 g |
| Water q.s. | 100 g |

The procedure is as follows:

The waxes are melted. The pigments are incorporated. The aqueous phase containing the preservatives, gum and keratin hydrolysate is heated to the same temperature as the waxy phase. The two phases are mixed and stirred vigorously. A dark blue mascara cream is obtained.

We claim:

1. Product in powder form consisting of particles, the particles being inorganic or organic particles less than 200 microns in size, the product containing, in or on the particles or in and on the particles, an indoline-based product obtained by oxidative polymerization employing an indoline, the indoline corresponding to the formula

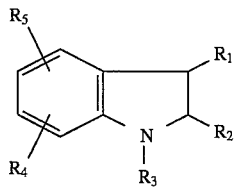

(I)

in which:

$R_1$ and $R_3$ represent, independently of one another, a hydrogen atom or a $C_1$–$C_4$ alkyl group;

$R_2$ represents a hydrogen atom, a $C_1$–$C_4$ alkyl group, a carboxyl group, a $C_1$–$C_4$ a alkoxy carbonyl group, or an n-alkylamino radical;

$R_4$ denotes a hydrogen atom, a $C_1$–$C_4$ alkyl group, a hydroxyl group, a $C_1$–$C_4$ alkozy group, an amino group, a $C_1$–$C_{10}$ alkylamino radical or a halogen atom;

$R_5$ denotes a hydrogen atom, a hydrozyl group, a $C_1$–$C_4$ alkoxy group or an amino group;

at least one of the radicals $R_4$ or $R_5$ denoting a hydroxyl, alkoxy or amino group: with the proviso that when $R_5$ denotes an amino group, $R_4$ cannot denote an alkylamino radical: or $R_4$ and $R_5$ attached to the carbon atoms joined together form a $C_1$–$C_2$ alkylenedioxy ring, at positions 5 and 6;

as well as the cosmetically acceptable salts.

2. Product according to claim 1, wherein the indoline is selected from the group consisting of: 5,6-dihydroxyindoline, 6-hydroxy indoline, 5,6-methylenedioxyindoline, 7-methoxy-6-hydroxy indoline, 6,7-dihydroxyindoline, 5-hydroxy-4-methoxy indoline, 4,5-dihydroxyindoline, 5-methoxy-6-hydroxy indoline, 4-hydroxy-5-methoxyindoline, 5-hydroxy-6-methoxy indoline, 4,7-dihydroxyindoline, 6-aminoindoline, N-ethyl-4-hydroxyindoline, 1-ethyl-6-amino-indoline, 5,6-diaminoindoline, 1-methyl-6-aminoindoline, 2-methyl- 6-aminoindoline, 3-methyl-6-aminoindoline, 2-methyl-5,6diaminoindoline, 5-chloro-7-aminoindoline, 3-methyl-5,7diaminoindoline, 5,7-diaminoindoline, 2-methyl-5,7-diaminoindoline, 7-aminoindoline, 2-methyl-7-amino indoline, 4-aminoindoline, 4-amino-6-chloroindoline, 4-amino- 6-iodoindoline, 4-amino-5-bromoindoline, 4-amino-5-hydroxyindoline, 4-amino-7-hydroxyindoline, 4-amino-5-methoxyindoline, 4-amino-7-methoxyindoline, 5-amino indoline, 2,3-dimethyl-5-aminoindoline, 1-methyl-5-aminoindoline, 2-methyl-5-aminoindoline, 5-[N-(1-methyl hexyl)amino]indoline, 5,6-dimethoxyindoline and 5,6-dihydroxy-2-carboxyindoline.

3. Product according to claims 1 or 2, wherein in that the indoline-based product results from the oxidative polymerization of at least one indoline as defined in claim 1 and at least one indole selected from the group consisting of monohydroxyindoles, dihydroxyindoles and aminoindoles.

4. Product according to claim 3, wherein the indoles have the formula:

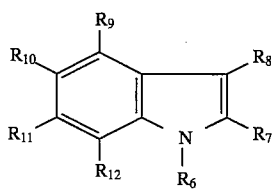

(II)

in which:

$R_6$ and $R_8$ denote, independently of one another, a hydrogen atom or a $C_1$–$C_4$ alkyl group;

$R_7$ represents a hydrogen atom, a $C_1$–$C_4$ alkyl group, a carboxyl group or a ($C_1$–$C_4$ alkoxy) carbonyl group;

$R_9$ and $R_{12}$ denote, independently of one another, a hydrogen atom, a hydroxyl group, a $C_1$–$C_4$ alkyl, amino, ($C_1$–$C_4$ alkoxy), ($C_2$–$C_4$ acyl)oxy or ($C_2$–$C_4$ acyl) amino group;

$R_{10}$ denotes hydrogen, a hydroxyl, ($C_1$–$C_4$alkoxy), ($C_1$–$C_4$ alkyl), halogen, amino, ($C_2$–$C_{14}$ acyl)oxy, ($C_2$–$C_4$ acyl)amino or trimethylsilyloxy group;

$R_{11}$ denotes hydrogen or a hydroxyl, ($C_1$–$C_4$ alkoxy), amino, ($C_2$–$C_4$ acyl)oxy, ($C_2$–$C_4$ acyl)amino, trimethylsilyloxy or hydroxy($C_2$–$C_4$ alkyl)amino group;

$R_{10}$ and $R_{11}$, together with the carbon atoms to which they are attached, can form a methylenedioxy ring optionally substituted with a $C_1$–$C_4$ alkyl, $C_1$–$C_4$ alkoxy group or a carbonyldioxy ring;

at least one of the groups $R_9$ to $R_{12}$ represents a group OZ or NHR, not more than one of the groups $R_9$ to $R_{12}$ denoting NHR;

and not more than two of the groups $R_9$ to $R_{12}$ denote OZ, in the case where Z denotes hydrogen, these groups are at positions 5 and 6;

and at least one of the groups $R_9$ to $R_{12}$ represents hydrogen, in the case where only one of these groups denotes hydrogen, only one group from among $R_9$ to $R_{12}$ then denotes NHR or OZ and the other groups denote $C_1$–$C_4$ alkyl; R in NHR denoting a hydrogen atom or a $C_2$–$C_4$ acyl or $C_2$–$C_4$ hydroxyalkyl group, and Z in OZ denoting a hydrogen atom or a $C_2$–$C_{14}$ acyl, $C_1$–$C_4$ alkyl or trimethylsilyl group; and the corresponding salts.

5. Product according to claim 1 wherein inorganic or organic particles are selected from the group consisting of lamellar or non-lamellar inorganic particles and lamellar or non-lamellar organic particles, the inorganic or organic particles being colored or uncolored, these particles having an average particle size of between 0.01 and 200 microns.

6. Product according to claim 1 wherein the non-lamellar inorganic particles are inert inorganic particles having a particle size of less than 20 microns.

7. Product according to claim 6, wherein the non-lamellar inorganic particles are calcium carbonate, silica or titanium oxide particles.

8. Product according to claim 1, wherein the particles are inorganic or organic lamellar particles which take the form of lamellae, the ratio of the largest dimension to the thickness being between 2 and 100 and the largest dimension being less than 50 microns.

9. Product according to claim 8, wherein the lamellar particles are selected from the group consisting of L-lauroyllysine, microparticles of ceramic which are optionally coated with zirconiumpowder, lamellar titanium dioxide, lamellar talc, boron nitride, lamellar mica, bismuth oxychloride and transparent red iron oxide.

10. Product according to claim 1 wherein the particles are colored inorganic particles consisting of metal salts which are insoluble in the cosmetic medium having a particle size of between 0.01 and 150 microns.

11. Product according to claim 10 wherein the colored inorganic particles are selected from the group consisting of iron oxides, ultramarine blue, chromium oxides, manganese violet and Prussian blue.

12. Product according to claim 1 wherein the particle is a nacreous or interference pigment having a particle size of between 10 and 150 microns.

13. Product according to claim 1, wherein the organic particles are non-lamellar organic particles having a particle size of less than 100 microns and which contain the indoline-based product at the surface or in the polymer network or at the surface and in the polymer network.

14. Product according to claim 13, wherein the particles of polymers are selected from the group comprising of:

a) polymers derived from keratin or hydrolyzed keratin;

b) silk fibroins;

c) chitin or chitosan;

d) microcrystalline cellulose;

e) synthetic polymers selected from the group consisting of:
  (i) polyethylene, polypropylene, polystyrene and poly(methyl methacrylate) which is optionally crosslinked;
  (ii) crosslinked poly-β-alanine;
  (iii) styrene/divinylbenzene, methyl methacrylate/ethylene glycol dimethyacrylate and vinyl stearate/divinylbenzene crosslinked polymers;
  (iv) hollow microspheres of the copolymer of vinylidene chloride and acrylonitrile;
  (v) porous microspheres of polyamide 12, polyamide or copolyamide 6/12; and
  (vi) silicone powder consisting of gums, resins and organosiloxane elastomers.

15. Cosmetic composition, comprising a product as defined in claim 1 in the form of a lotion, thickened lotion, gel, cream, milk, powder, stick, or aerosol.

16. Composition according to claim 15, for making up the skin, hair, nails, eyelashes and eyebrows, in anhydrous, aqueous pasty, solid or liquid form.

17. Composition according to claim 15 for protecting the human epidermis against solar UV radiation, in the form of suspensions or dispersions in solvents or fats, or the form of emulsions, ointments, gels, solid sticks or aerosol foams.

18. Composition according to claim 15 containing fats, organic solvents, silicones, thickeners, demulcents, surfactants, sunscreen agents, antifoams, hydrating agents, perfumes, preservatives, antioxidants, fillers, sequestering agents, treatment agents, propellants, alkalinizing or acidifying agents or pigments.

19. Composition according to claim 15, wherein the powder in the form of inorganic or organic particles which contain the indoline-based product in or on the particles or in and on the particles is present in concentrations of between 0.05 and 35% by weight relative to the total weight of the composition.

20. Process for protecting the human epidermis, comprising applying the product as defined in claim 1.

21. Process for treating the skin, hair, nails, eyelashes or eyebrows, comprising applying the product as defined in claim 1 in makeup.

* * * * *

UNITED STATES PATENT AND TRADEMARK OFFICE
CERTIFICATE OF CORRECTION

PATENT NO. : 5,496,543
DATED : March 5, 1996
INVENTOR(S) : LAGRANGE et al

It is certified that error appears in the above-identified patent and that said Letters Patent is hereby corrected as shown below:

On the Title page, PCT Data should read as follows:
    [22]  PCT Filed:  January 13, 1993

Signed and Sealed this

Eleventh Day of June, 1996

Attest:

BRUCE LEHMAN

Attesting Officer    Commissioner of Patents and Trademarks